United States Patent [19]
Trudell et al.

[11] Patent Number: 5,158,545
[45] Date of Patent: Oct. 27, 1992

[54] DIAMETER EXPANSION CANNULA

[75] Inventors: Leonard A. Trudell, East Greenwich, R.I.; Anthony D. Whittemore, Sherborn, Mass.

[73] Assignee: Brigham and Women's Hospital, Boston, Mass.

[21] Appl. No.: 694,949

[22] Filed: May 2, 1991

[51] Int. Cl.⁵ .............................................. A61M 31/00
[52] U.S. Cl. ...................................... 604/53; 604/104; 604/164; 604/280; 606/198
[58] Field of Search ............... 604/96, 104, 164, 166, 604/171, 172, 264, 280, 281, 52, 53, 158, 161; 606/108, 191, 194, 198; 623/1, 12

[56] References Cited

U.S. PATENT DOCUMENTS

| Re. 31,855 | 3/1985 | Osborne . | |
|---|---|---|---|
| 3,509,883 | 5/1970 | Dibelius . | |
| 3,996,938 | 12/1976 | Clark, III . | |
| 4,175,564 | 11/1979 | Kwak . | |
| 4,411,655 | 10/1983 | Schreck . | |
| 4,412,832 | 11/1983 | Kling et al. . | |
| 4,580,568 | 4/1986 | Gianturco . | |
| 4,650,466 | 3/1987 | Luther . | |
| 4,655,771 | 4/1987 | Wallsten . | |
| 4,687,470 | 8/1987 | Okada . | |
| 4,710,181 | 12/1987 | Fugua | 604/280 |
| 4,733,665 | 3/1988 | Palmaz . | |
| 4,738,666 | 4/1988 | Fugua | 604/280 |
| 4,739,762 | 4/1988 | Palmaz . | |
| 4,808,164 | 2/1989 | Hess . | |
| 4,830,003 | 5/1989 | Wolff et al. | 623/1 X |
| 4,865,593 | 9/1989 | Ogawa et al. . | |
| 4,885,003 | 12/1989 | Hillstead . | |
| 4,921,484 | 5/1990 | Hillstead . | |
| 4,954,126 | 9/1990 | Wallstén . | |
| 5,019,090 | 5/1991 | Pinchuk | 606/194 |
| 5,026,377 | 6/1991 | Burton et al. | 606/108 |
| 5,064,435 | 11/1991 | Porter | 623/12 |
| 5,071,407 | 12/1991 | Termin et al. | 604/104 |

Primary Examiner—C. Fred Rosenbaum
Assistant Examiner—C. Maglione
Attorney, Agent, or Firm—Sterne, Kessler, Goldstein & Fox

[57] ABSTRACT

The present invention is a diameter expansion cannula apparatus which is used to establish fluid flow to a healthy blood vessel or to a diseased blood vessel. The cannula apparatus has a cannula which is coated with silicone and is formed of a braided construction which provides the cannula with an inherent resilience, yet allows the length of the cannula to become longer and the diameter of the cannula to become narrower when tension is applied along the longitudinal axis of the cannula. A peelable sheath is used to maintain the cannula in its elongated narrow state during insertion into a blood vessel. Removal of the sheath allows the cannula to return to its pre-tensioned diameter, thereby providing a radial force upon any obstruction within the blood vessel. The cannula apparatus is a self-contained unit which includes a sharpened point on the end of a balloon catheter to puncture the blood vessel of a patient and to assist the cannula in returning to its pre-tensioned diameter if any obstruction within the blood vessel prevents the cannula from returning to its pre-tensioned diameter.

16 Claims, 6 Drawing Sheets

DIAMETER EXPANSION CANNULA

FIELD OF THE INVENTION

The present invention relates generally to a flexible cannula used to permit fluid flow to and from a normal or a diseased blood vessel of a patient and more particularly to a flexible cannula that has an expandable diameter.

BACKGROUND OF THE INVENTION

Various apparatus and methods for creating a passageway to a blood vessel are readily available; these apparatus and methods often involve the use of a cannula. The conventional cannula has the role of securing a passageway into a blood vessel to permit either the release of substances from the body or the injection of substances into the body. The processes of introducing a cannula into the body is called cannulation. The term cannula has been chosen in discussing the invention. However, the term catheter could be substituted as they are equivalent terms in the context of this invention.

Cannulation of a blood vessel, such as a vein or an artery, is a particularly delicate process because of the danger of damage to the blood vessel such as puncture or abrasion caused by the application of excessive force. Therefore, a number of devices and methods of using such devices have been developed to cannulate blood vessels while minimizing damage to the blood vessel.

Two examples of known cannulation procedures are described in U.S. Pat. No. Re 31,855 to Osborne (the Osborne patent). The first cannulation procedure described in the Osborne patent involves multiple exchanges of elements inserted into a blood vessel. The procedure involves the direct insertion of a rigid, hollow needle into a blood vessel, passing a guidewire through the needle, withdrawing the needle, passing a cannula over the guidewire and withdrawing the guidewire leaving just the cannula in place. The second cannulation procedure described in the Osborne patent involves the insertion of a rigid needle and cannula simultaneously into a blood vessel, and withdrawing the needle leaving the cannula in place. The cannula may be removed from the patient by pulling tabs disposed on the cannula, causing the cannula to tear in a longitudinal direction as it is removed.

One particular problem encountered during cannulation arises when the blood vessel is diseased in some way thereby reducing the flow path through the blood vessel and preventing proper cannulation. One possible solution to this problem involves the introduction of a catheter into the blood vessel which can assist the diameter of the blood vessel in returning to its pre-diseased diameter thereby increasing the fluid flow through the blood vessel. One example of a device which increases the diameter of a blood vessel is described in U.S. Pat. No. 4,921,484 to Hillstead (the Hillstead patent). The device described in the Hillstead patent is a steel mesh balloon attached to a catheter. The balloon is inserted into a blood vessel and is advanced to a desired point within the circulatory system. Expansion of the balloon widens the diameter of the blood vessel, thereby widening the flow path through the vessel. The purpose of this device is to dilate a blood vessel within the circulatory system. Therefore, the device is not configured to provide and maintain a widened flow path into, out of and through a diseased or a normal blood vessel.

Another example of a device used to maintain a widened flow path through a blood vessel is an endovascular stent. Stents are often used at a distant site in the body as a substitution for a vascular graft (usually in the aorta). One example of an endovascular stent is found in U.S. Pat. No. 4,580,568 to Gianturco (the Gianturco patent). The stent described in the Gianturco patent is positioned in a passageway in the cardiovascular system after first being compressed in a sheath which retains the stent in a compressed state. After the stent is properly positioned within the passageway, the sheath is withdrawn, thereby allowing the stent to expand to its pre-compressed configuration. As long as the stent is maintained within the blood vessel, a cannula cannot be inserted through the area within the blood vessel containing the stent. Hence, a cannula cannot be used simultaneously with the stent to properly cannulate a blood vessel.

SUMMARY OF THE INVENTION

It is with these problems of the related art in mind that the present invention was developed. The present invention not only overcomes the problems of the above-noted devices and methods, but furthermore, has many advantages not previously achieved in known devices and methods of cannulation.

It is an object, therefore, of the instant invention to provide a self-contained, diameter-expansion cannula apparatus capable of creating and maintaining a flow path into a normal or diseased blood vessel.

It is the further object of the instant invention to provide a self-contained, diameter-expansion cannula apparatus which achieves the aforementioned object without requiring the exchange of elements within the cannula apparatus or the replacement of the entire apparatus.

It is another object of the instant invention to provide a self-contained, diameter-expansion cannula apparatus having an ultra-low profile during insertion into a blood vessel.

It is another object of the instant invention to provide a self-contained, diameter-expansion cannula which has a cannula body having inherently resilient characteristics beneficial for diameter-expansion of blood vessels.

It is another object of the instant invention to provide a self-contained, diameter-expansion cannula apparatus which is relatively easy to manufacture.

The present invention is directed to a diameter-expansion cannula apparatus which is used to establish fluid flow into and out of normal or a diseased blood vessel. The cannula apparatus has a cannula body formed of a braided construction which allows the length of the cannula to become longer and the diameter of the cannula to become narrower when tension is applied along the longitudinal axis of the cannula. A removable sheath is used to maintain the cannula in its elongated, narrow configuration thereby providing the cannula with an ultra-low profile during insertion into a blood vessel. Removal of the sheath after cannulation of the blood vessel allows the cannula to return to its pre-tensioned configuration, thereby providing a radial force upon any obstruction in that region of the blood vessel. The cannula apparatus is a self-contained unit in that it includes means for puncturing the skin and blood vessel to access the same. In particular, the cannula apparatus may include a balloon catheter with a sharpened point to puncture the blood vessel of a patient. The balloon catheter may also assist the cannula in returning to its pre-tensioned configuration despite any obstructions within the blood vessel. The balloon catheter also acts as a plug preventing fluid from flowing through the cannula apparatus during insertion.

Additionally, the present invention may also be characterized as a method for cannulating a blood vessel, comprising the steps of: causing a cannula to be tensioned into a narrow configuration, disposing a sheath around the tensioned cannula to maintain its narrow configuration, puncturing the blood vessel while simultaneously inserting the cannula into the patient through the puncture, and removing the sheath from the cannula thereby allowing the cannula to expand back to its pre-tensioned configuration. The method may further comprise the steps of inserting a balloon catheter into the cannula prior to puncturing the blood vessel. The method may also comprise the step of inflating the balloon catheter after removing the sheath to assist the catheter in returning to its pre-tensioned state. Furthermore, the method may comprise the steps of deflating and removing the balloon catheter after a widened flowpath is established into, out of and through a diseased or a normal blood vessel to permit fluid flow through the cannula.

BRIEF DESCRIPTION OF THE DRAWINGS

The foregoing and other objects, aspects and features of the present invention will be more fully appreciated as the same becomes better understood when considered in conjunction with the detailed description of the present invention viewed in conjunction with the accompanying drawings in which.

DETAILED DESCRIPTION OF THE PREFERRED EMBODIMENT

Referring now to the drawings, a preferred embodiment of the invention is shown. The present invention comprises a cannula apparatus and a cannulating procedure for establishing fluid flow to a blood vessel of a patient (patient, as used herein, refers to all animal species). As discussed in greater detail below, both the apparatus and its attendant method of use are particularly useful in establishing fluid flow to a diseased blood vessel by exerting a radial force against any obstruction, thereby widening the flow path through the vessel while maintaining the cannula in place at its point of entry.

Figure 1:
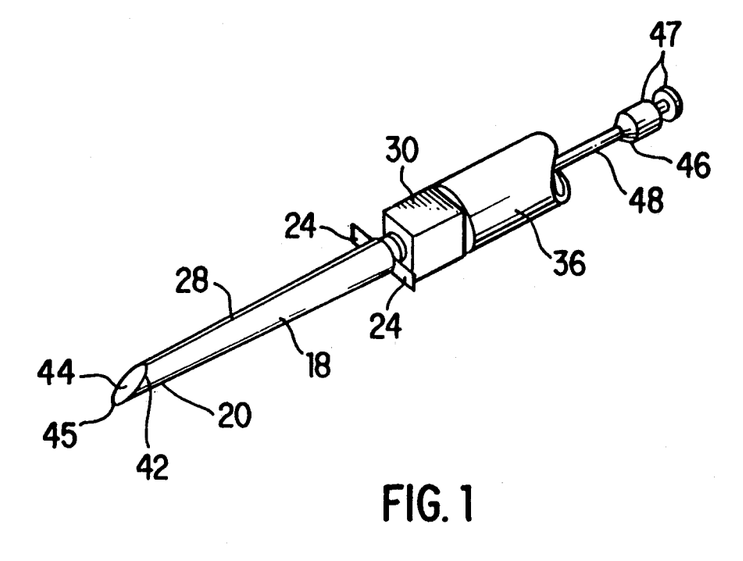
FIG. 1 is a perspective view of the cannula apparatus of the present invention.
Figure 2:
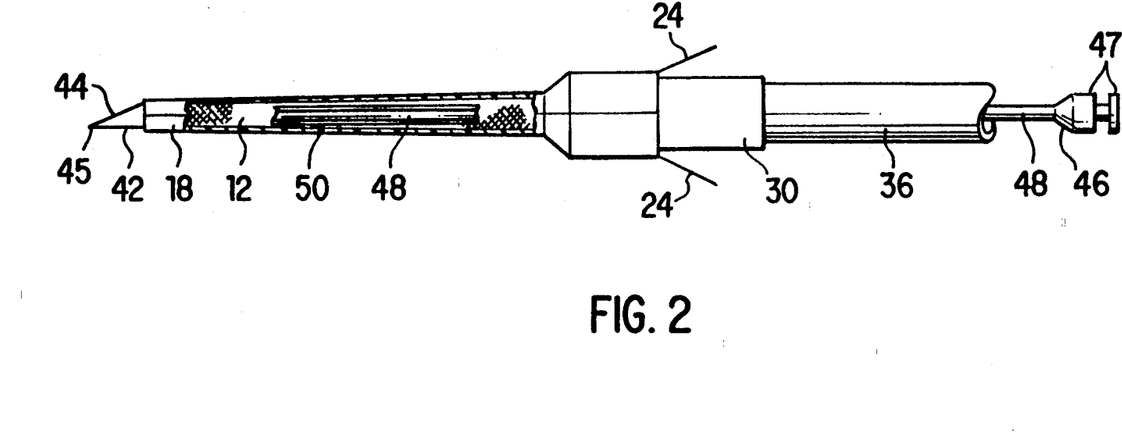
FIG. 2 is a partially cut away side view of the cannula apparatus of FIG. 1.
Figure 3:
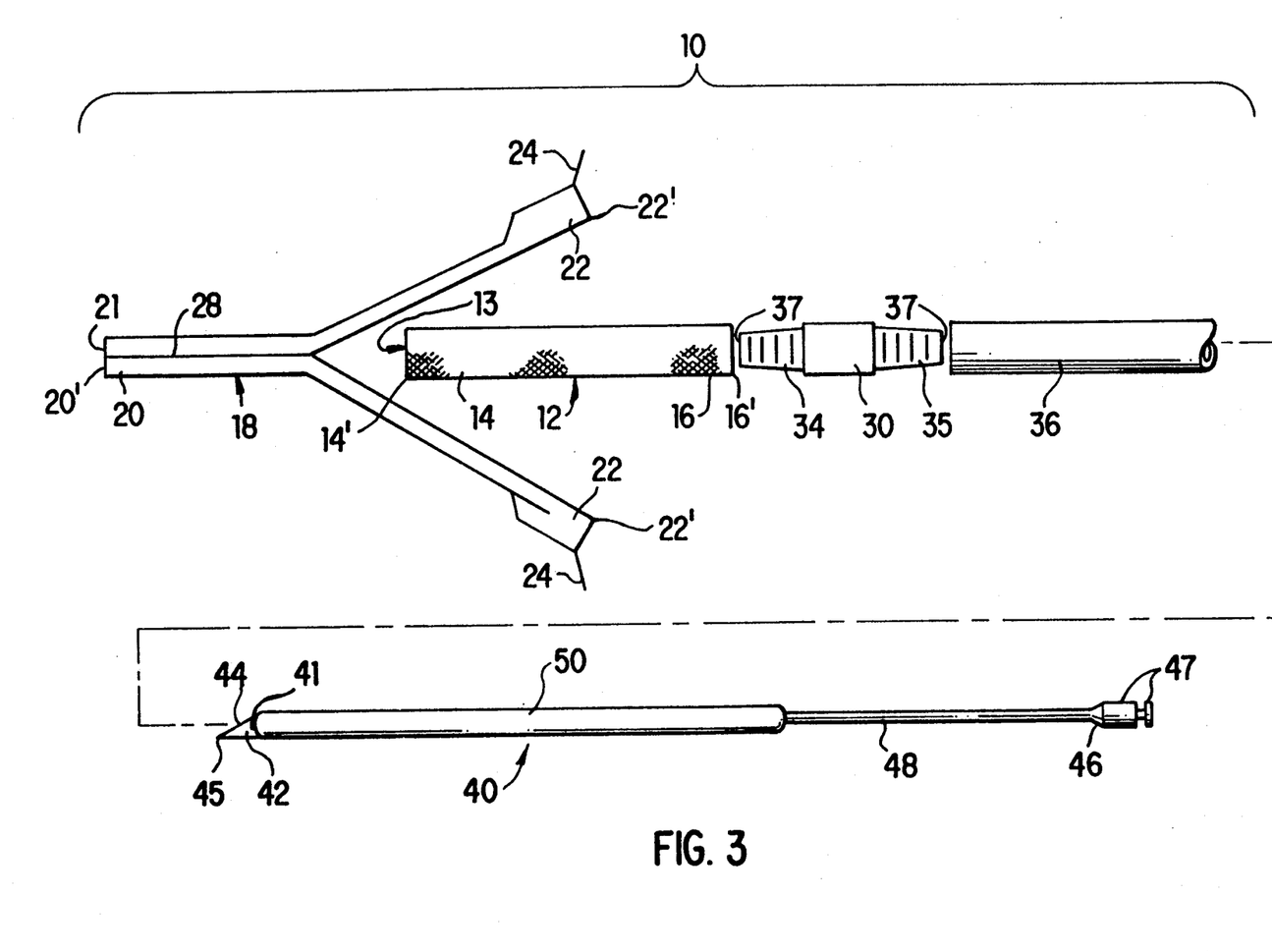
FIG. 3 is an exploded side view of the apparatus of FIG. 1.

Turning first to FIGS. 1, 2 and 3, the cannula apparatus, shown generally at 10, is used to establish fluid flow to or from the blood vessel of a patient. As best seen in FIG. 3, cannula apparatus 10 generally comprises four basic components: a cannula shown generally at 12, a sheath shown generally at 18, a connector shown generally at 30 and a balloon catheter shown generally at 40, each of which will now be described in more detail.

With continuing reference to FIG. 3, cannula 12 will now be described in greater detail. Cannula 12 is of a hollow cylindrical configuration having a distal end 14, a distal edge 14', a proximal end 16 and a proximal edqe 16' (distal as used throughout this specification refers to the portion of the device furthest from the user; proximal refers to the portion of the device closest to the user). Preferably, cannula 12 has a slightly conical shape, tapering from proximal end 16 to distal end 14. Alternatively, cannula 12 may have any geometrically-shaped configuration provided that it is compatible with the blood vessel of a patient and that fluid may be passed therethrough.

Cannula 12 has a internal lumen 13 which may also preferably have a cylindrical configuration. However, any other geometrically shaped configuration may be suitable. Cannula 12 is formed of a braided helix construction composed of several individual yarns or filaments extending in a helix configuration with the longitudinal center line of cannula 12 as a common axis. This braided construction provides cannula 12 with an inherent resilience which allows the length of cannula 12 to become longer and the diameter of cannula 12 to become narrower when tension is applied along the longitudinal axis of the cannula. That is, when the distal end 14 and proximal end 16 are pulled in opposite directions from each other (along the longitudinal axis of the cannula) cannula 12 becomes temporarily longer and narrower. When tension is released, cannula 12 returns to its original configuration.

In the preferred embodiment, cannula 12 is formed of thermoplastic filaments which are capable of being heat-set in a predetermined length and width, such that even after tension is applied to the cannula to lengthen and narrow it, upon release of the tension, the cannula 12 returns to substantially the predetermined, heat-set configuration. This allows the cannula to be tensioned and its diameter reduced to an ultra-low profile for easy introduction into the blood vessel of a patient, when tension is released, cannula 12 returns to its predetermined diameter even while inside the blood vessel. This procedure is described in greater detail below.

Cannula body 12 is intended to carry fluid into and out of a blood vessel of a patient. Therefore, it is preferably coated with a substance such as silicone or other water-impervious substance, to minimize fluid leakage along the length of cannula 12. In the preferred embodiment, cannula 12 is made of a braided material manufactured by Bentley Harris of Lyonville, Pa., available as Part No. 6747001, and sold under the name "EXPANDO PT."

With continuing reference to FIG. 3, sheath 18 is shown. Sheath 18 is of a hollow cylindrical configuration having a distal end 20, a distal edge 20', a proximal end 22 and a proximal edge 22'. Preferably, sheath 18 has a slightly conical shape. However, sheath 18 may have any geometrically-shaped configuration provided that the chosen configuration is compatible with the blood vessel of a patient. Sheath 18 has an internal lumen 21 which may also have a cylindrical configuration or any other suitable configuration which preferably conforms to the geometric shape of cannula 12. The lumen 21 preferably has a diameter slightly larger than the exterior diameter of cannula 12 in its tensioned configuration. In use, sheath 18 is disposed around cannula 12 such that distal end 20 of sheath 18 is disposed around distal end 14 of cannula 12 and proximal end 22 of sheath 18 is disposed around proximal end 16 of cannula 12.

As best seen in FIG. 1, sheath 18 has a first score line 28 extending longitudinally from proximal edge 22' to distal edge 20'. Also, a second score line (not shown) similar to score line 28 is oppositely facing first score line 28 and also extends longitudinally from proximal edge 22' to distal edge 20'. These score lines allow sheath 18 to separate into two pieces for easy removal by tearing the sheath along the score lines. Two tabs 24 are oppositely arranged on sheath 18. Each tab 24 is attached to a portion of sheath 18 between the two score lines on proximal end 22. Tabs 24 allow the user to grip the sheath to tear it in two, while simultaneously withdrawing it from the blood vessel.

Sheath 18 is preferably made of Teflon ® or other suitable material which is both flexible and peelable. One such suitable material is manufactured by Teleflex Medical, Jaffrey, N.H. and sold under the name Split Sheath/Dilator.

Although two score lines are preferred, a single score line may also be used. In addition, although score line 28 is shown as extending to distal edge 20', score line 28 and any additional score lines may terminate close to but before distal edge 20'. If only one score line is used, tabs 24 may be attached to a portion of the sheath 18 adjacent the score line.

With continuing reference to FIG. 3, connector 30 is shown. Connector 30 has a center portion 31, a distal extension 34, and a proximal extension 35 which is received in tubing 36. Extensions 34 and 35 preferably have tapered, cylindrical configurations although any geometrically shaped configuration may be used provided that it is compatible with internal lumen 13 of cannula 12 and the hollow interior of tubing 36. Connector 30 has an internal lumen 37, which may also have a cylindrical configuration or any other suitable geometrically-shaped configuration provided that fluid may be passed therethrough. Connector 30 is preferably made of any suitable bio-medical plastic material through which body fluids and medicine may be safely passed. One suitable connector is manufactured of Polycarbonate, by Bentley Laboratories, Inc. of Irvine, Calif.

When diameter-expansion cannula apparatus 10 is assembled, distal extension 34 is partially disposed within lumen 13 of cannula 12. In addition, a portion of tubing 36 is disposed around the proximal extension 35 of connector 30. Tubing 36 may simultaneously be connected to an external device for providing or withdrawing substances through the cannula apparatus. One particular device for which the present invention finds utility is a circulatory support system. Tubing 36 is preferably any conventional flexible and leakproof medical tubing, such as Silastic ®.

With continuing reference to FIG. 3, balloon catheter 40 is shown. Balloon catheter 40 has a distal end 41 and a proximal end 46. A piercing tip 42 is disposed on distal end 41. Piercing tip 42 has a beveled edge 44 and a sharp point 45. A Luer ® hub 47 is disposed on proximal end 46 for connecting a syringe to the balloon catheter 40 for inflating the balloon 50. Inflatable balloon 50 preferably extends along approximately two-thirds the length of the entire catheter 40 running from the proximal extension 35 of connector 30 to the distal end 41 of catheter 40, circumscribing a central support 48 (as seen in FIG. 2). Central support 48 extends from distal end 41 to proximal end 46 and has an internal lumen (not shown).

With continuing reference to FIG. 2, balloon catheter 40 is shown as disposed within cannula 12, which is within sheath 18. Piercing tip 42 extends beyond distal end 14 of cannula 12 and distal end 20 of sheath 18. Preferably, distal end 41 of balloon catheter 40 is completely disposed within cannula 12. However, in the alternative, distal end 41 may extend beyond end 14 of cannula 12. Central support 48 extends through tubing 36, connector 30 and cannula 12. Central support 48 may also extend beyond the distal edge 14' of cannula 12 and the distal edge 20' of sheath 18.

The process of properly assembling and using the diameter-expansion cannula 10 will now be described. Preferably, the cannula is received by the hospital as an assembly similar to that shown in FIG. 1. That assembly, however, is formed by first heat-setting the cannula to a predetermined diameter. To accomplish this, the cannula 12 is fitted over a mandrel (not shown) and tensioned at opposite ends until its interior diameter closely hugs the mandrel. Sufficient heat is applied to set the filaments in the desired configuration. The heat-set cannula is then coated with silicone and is cured. The opposite ends of the cannula are pulled in opposite directions at which the length of the cannula increases while its diameter decreases from the heat-set dimensions. Sheath 18 is slipped over the tensioned cannula to retain the reduced diameter until the sheath is removed, preferably after the assembly is inserted into the body of a patient. The heat setting and application of the sheath can be accomplished on a fixed length of cannula as well as on a continuous length. Distal extension 34 of connector 30 is inserted into lumen 13 on the proximal end 16 of cannula 12. The proximal extension of connector 30 may then be inserted into tubing 36. Balloon catheter 40 may then be placed within tubing 36, connector 30 and cannula body 12 such that piercing tip 42 extends beyond distal edge 14' of cannula 12 and distal edge 20' of sheath 18. The diameter expansion cannula apparatus 10 is now ready for use.

The process of cannulating a blood vessel using the diameter expansion cannula apparatus 10 of the instant invention will now be described. During insertion of diameter-expansion cannula 10 into a patient, piercing tip 42 punctures the skin and blood vessel of the patient as well as any tissue located therebetween. Substantially simultaneously, the diameter-expansion cannula apparatus 10 is inserted into the patient through the skin puncture until the cannula 12 reaches the desired location within the blood vessel 52. Tabs 24 remain outside the patient.

Figure 4:
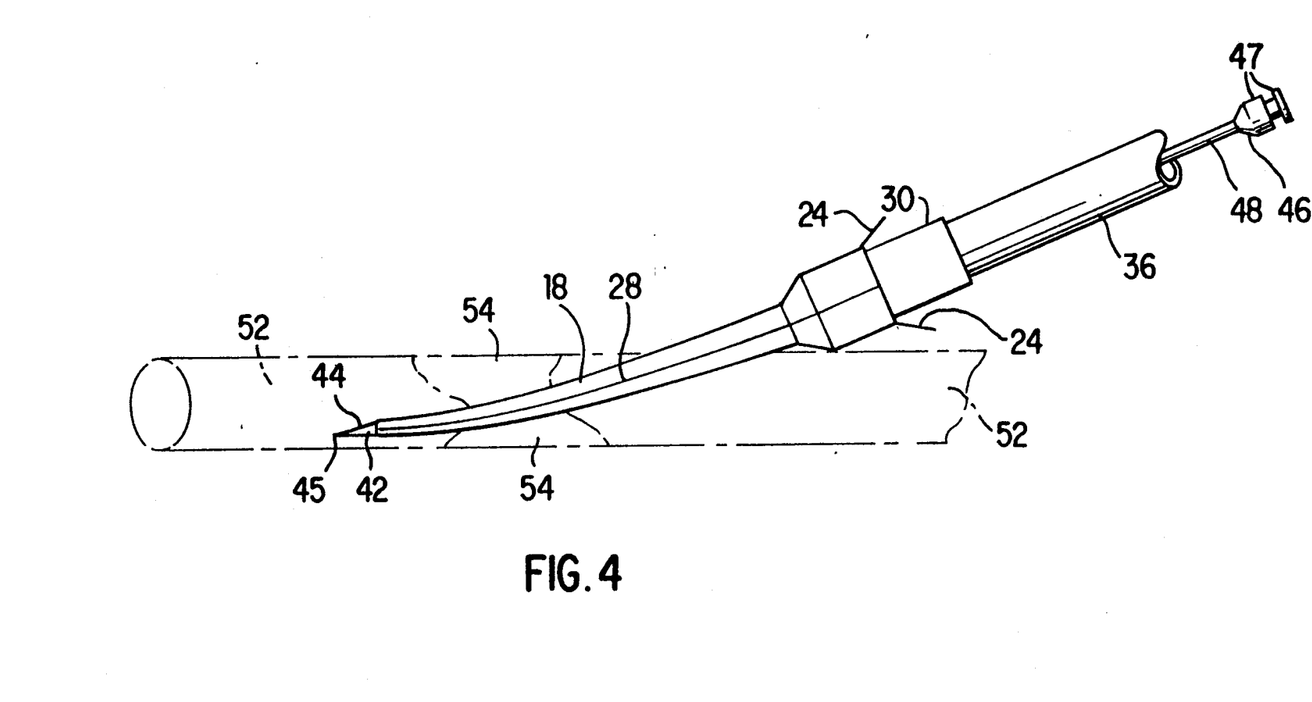
FIG. 4 shows the apparatus of FIG. 1 inserted into a diseased blood vessel.
Figure 5:
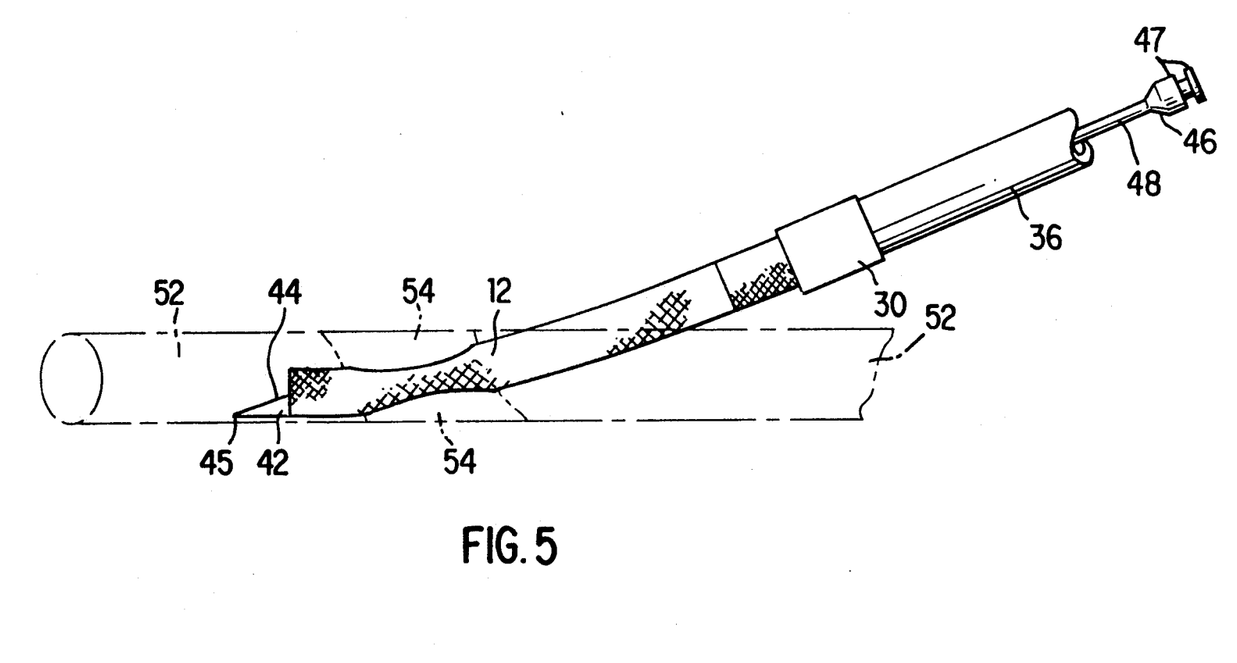
FIG. 5 is similar to FIG. 4 after removal of the sheath.

Referring now to FIG. 4, the diameter-expansion cannula 10 of the instant invention is shown after insertion into a diseased blood vessel 52. To increase the diameter of cannula 12, tabs 24 are pulled apart (as in FIG. 3) to initiate peeling along score line 28 and any additional score lines located on sheath 18. At the same time, sheath 18 is withdrawn from the blood vessel leaving cannula 12 within the patient. Upon removal of sheath 18, cannula 12 is allowed to expand back to its pre-tensioned, heat-set (original) configuration. However, if blockage 54 is significant it may prevent cannula 12 from returning to its original configuration. In this case, balloon catheter 40 may be used to assist expansion of cannula 12. To inflate balloon catheter 40, a syringe (not shown) is used to force air through central support 48 and into balloon 50. As balloon 50 inflates, it forces the diameter of cannula 12 to expand and, thus, eliminate obstruction 54 to increase the flowpath through the blood vessel 52.

Figure 6:
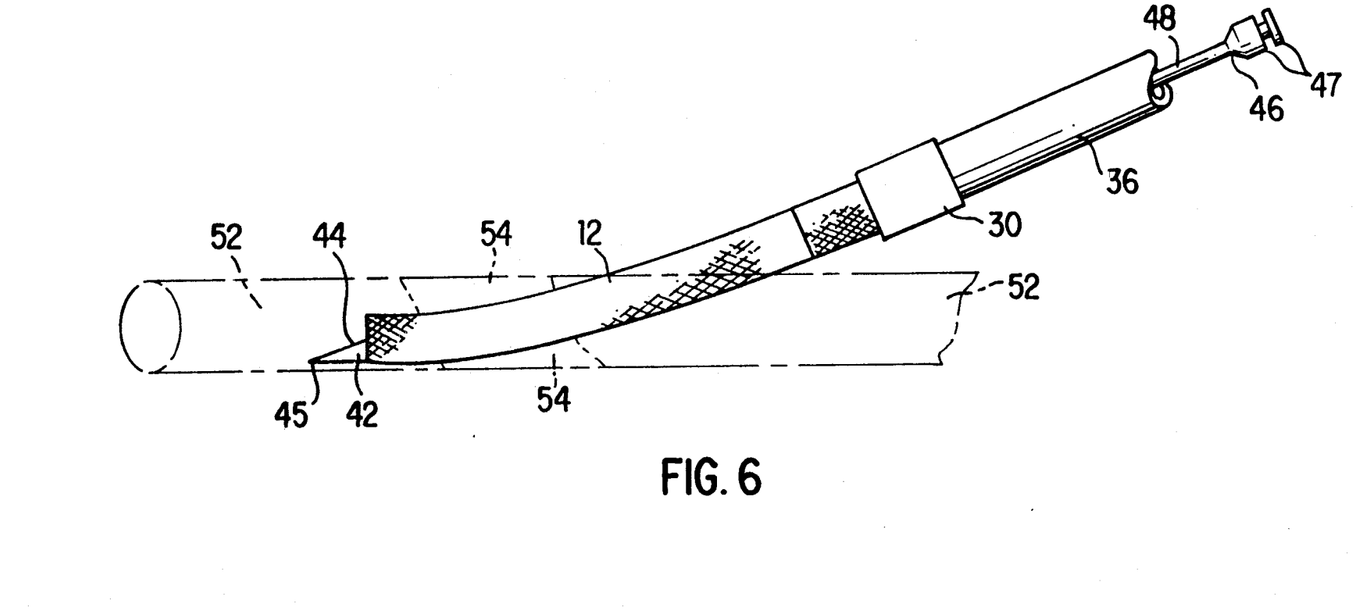
FIG. 6 is similar to FIG. 5 after the cannula returns to its pre-tensioned configuration.

FIG. 6 shows cannula 12, returned to its original configuration through its inherent resilience and the assistance of balloon catheter 40. The cannulation process may then be completed by deflating and removing balloon catheter 40 leaving a near normal flowpath to and from blood vessel 52 thus completing the cannulation process. The inherent resilience of the braided construction of cannula 12 provides a constant radial force against blockage 54 thereby maintaining a flow path through blood vessel 52. Once cannulation is complete, fluid may be passed through the cannula 12 either to exit or to enter blood vessel 52.

The principles, preferred embodiments, and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the invention. Accordingly, the foregoing detailed description should be considered exemplary in nature and not limited to the scope and spirit of the invention as set forth in the attached claims.

We claim:

1. An apparatus for expanding the diameter of a blood vessel of a patient comprising:
   a cannula for passing fluid into and out of a blood vessel of a patient, said cannula having a proximal end and a distal end defining a predetermined length and diameter, formed of a braided construction which allows the length of said cannula to become longer and the diameter of said cannula to become narrower when tension is applied along the longitudinal axis of said cannula;
   means disposed adjacent said distal end of said cannula for puncturing the blood vessel of a patient to permit insertion of said cannula into said blood vessel;
   a removable sheath disposed over said cannula when tension is applied thereto such that the length of said cannula is longer and the diameter is narrower, whereby said sheath maintains the tensioned length and diameter of said cannula during insertion into the patient, whereby said cannula body is allowed to return to its predetermined length and diameter upon removal of said sheath from said cannula.

2. The apparatus of claim 1 further comprising:
   a connector disposed adjacent said proximal end of said cannula; and
   tubing connected to said connector.

3. The apparatus of claim 1 wherein said cannula is coated with a substance to minimize leakage of fluid from said cannula.

4. The apparatus of claim 1 further comprising:
   means disposed within said cannula for preventing fluid flow through said cannula while it is being inserted within said blood vessel.

5. The apparatus of claim 4 wherein said means for preventing fluid flow comprises a balloon catheter.

6. The apparatus of claim 5 wherein said balloon catheter is removable from said cannula.

7. The apparatus of claim 5 wherein said means for puncturing is integral with said balloon catheter.

8. The apparatus of claim 1 wherein said sheath has a tab for initiating removal of said sheath from said cannula, said tab being disposed on said proximal end of said sheath.

9. The apparatus of claim 8 wherein said sheath contains a score line, wherein said score line permits said sheath to be peeled away from said cannula body.

10. The apparatus of claim 9 wherein said sheath contains two substantially parallel score lines extending from said proximal end of said sheath adjacent said tab toward said distal end of said sheath.

11. The apparatus of claim 1 wherein said means for puncturing includes a sharp piercing tip.

12. The apparatus of claim 1 wherein said means for puncturing extends beyond said cannula.

13. A method of cannulating a blood vessel of a patient comprising:
   causing a cannula to be tensioned along its longitudinal axis into a narrow state;
   disposing a sheath around said tensioned cannula to maintain said narrow state;
   puncturing the blood vessel and simultaneously inserting said cannula into said patient through said skin puncture;
   removing said sheath from said cannula thereby allowing said cannula to expand back to a pre-tensioned state; and
   passing fluid through said cannula.

14. The method of claim 13 further comprising the steps of:
   inserting a balloon catheter into said cannula prior to puncturing the blood vessel and inserting said cannula into said blood vessel.

15. The method of claim 14 further comprising the steps of:
   inflating said balloon catheter after removing said sheath to assist said cannula in returning to its pre-tensioned state.

16. The method of claim 15 further comprising the steps of:
   deflating said balloon catheter; and
   removing said balloon catheter to permit fluid flow through said cannula.

* * * * *